United States Patent [19]

Herrmann et al.

[11] Patent Number: 5,517,991

[45] Date of Patent: May 21, 1996

[54] UROLOGICAL WORKSTATION

[75] Inventors: Klaus Herrmann, Nuremberg; Guenther Krauss, Erlangen, both of Germany

[73] Assignee: Siemens Aktiengesellschaft, Munich, Germany

[21] Appl. No.: 272,592

[22] Filed: Jul. 11, 1994

[30] Foreign Application Priority Data

Jul. 27, 1993 [DE] Germany .......................... 43 25 214.1

[51] Int. Cl.[6] ..................................................... A61B 6/00
[52] U.S. Cl. ............................. 128/653.1; 601/2; 601/4; 5/601; 378/209
[58] Field of Search ................... 128/653.1, 660.03; 601/2–4; 5/601; 378/209; 607/97

[56] References Cited

U.S. PATENT DOCUMENTS

| 4,526,168 | 7/1985 | Hassler et al. . |
| 4,674,505 | 6/1987 | Pauli et al. . |
| 5,395,299 | 3/1995 | Hermann et al. . |

FOREIGN PATENT DOCUMENTS 9304457  7/1993  Germany .

Primary Examiner—Ruth S. Smith
Attorney, Agent, or Firm—Hill Steadman & Simpson

[57] ABSTRACT

A urological workstation has a patient support table with a support plate having a length which does not significantly exceed 145 cm, and an x-ray diagnostics installation that is adjustable relative to the patient support table. The x-ray diagnostics installation is adjustable relative to the patient support table such that its central ray is shifted along the longitudinal axis of the support table through positions which are parallel to each other.

5 Claims, 2 Drawing Sheets

1
UROLOGICAL WORKSTATION

BACKGROUND OF THE INVENTION

1. Field of the Invention

The present invention is directed to a urological workstation of the type having a patient support table whose length does not significantly exceed 145 cm, and an x-ray diagnostics installation.

2. Description of the Prior Art

In urological workstations of the type described above, the patient support table is usually adjustable in the direction of its longitudinal axis and transversely relative thereto in order to be able to examine different regions of a patient with the x-ray diagnostics installation (see German Utility Model 93 04 457). Since the patient is frequently placed on the patient support table in the so-called lithotomy position, i.e. lying on his back with legs spread and bent at the hip and knee joints, and the urologist assumes a seated position between the legs of the patient, an adjustment of the patient support table causes a dislocation of the patient relative to the urologist, who must then either correct his own position or assume an unnatural posture. Both are uncomfortable for the urologist.

SUMMARY OF THE INVENTION

An object of the present invention is to fashion a urological workstation of the type initially described which permits the urologist to work comfortably.

This object is achieved in a urological workstation constructed in accordance with the present invention having a patient support table/, *whose length does not significantly exceed 145 cm (i.e., the length along the longitudinal axis is less than or equal to approximately 145 cm), and an x-ray diagnostics installation that is adjustable relative to the patient support table so that its central ray is shifted along the longitudinal axis of the patient support table while remaining parallel to its original position. It is thus possible to examine different regions of the patient with the x-ray diagnostics installation without requiring a displacement of the patient support table. Even when the urologist wishes to examine different regions of the patient during his work, the urologist can thus remain in a comfortable working position once it has been found.

*for a patient to undergo a urological procedure (i.e. to be examined and/or undergo treatment)

Since it is expedient for good accessibility to the patient for the urologist to position the patient on the support table such that the patient's perineum is located directly above the edge of one end of the patient support table that limits the patient support table in the longitudinal direction, it is possible in a version of the invention to adjust the x-ray diagnostics installation into a first final position wherein its central ray proceeds through an edge of a first end of the patient support table that limits the patient support table in longitudinal direction.

Proceeding from the first final position, the x-ray diagnostics installation is adjustable into a second final position in the direction toward the other end edge of the patient support table, the central ray of the x-ray diagnostics installation in the second final position is at a distance of not significantly less than 22 cm from the edge of the first end of the patient support table, as measured in the direction of the longitudinal axis of the patient support table. In this position, a gap-free examination of the entire urogenital tract is possible without requiring a dislocation of the patient.

In a preferred embodiment of the invention, the urological workstation also includes a therapy means, whereby the x-ray diagnostics means serves as locating means for locating a region to be treated with the therapy means. In particular, a source of acoustic waves is provided as the therapy means. When this is a shockwave source, there is the possibility of treating stone maladies. It is expedient in this context when the x-ray diagnostics installation proceeding from the first final position in the direction toward the other end edge of the patient support table is adjustable into a second final position wherein its central ray has a distance of not significantly less than 54 cm from the edge of the first end of the patient support table as measured in the direction of the longitudinal axis of the patient support table. In this position, the gallbladder can be examined with the x-ray diagnostics installation in conjunction with the treatment of gallstone conditions without dislocating the patient and, for example, gallstones can be located.

When a therapeutic ultrasound source is provided as the source of acoustic waves, there is the possibility of treating pathological tissue changes, for example tumors or benign prostate hyperplasia.

DESCRIPTION OF THE PREFERRED EMBODIMENTS

Figure 1:
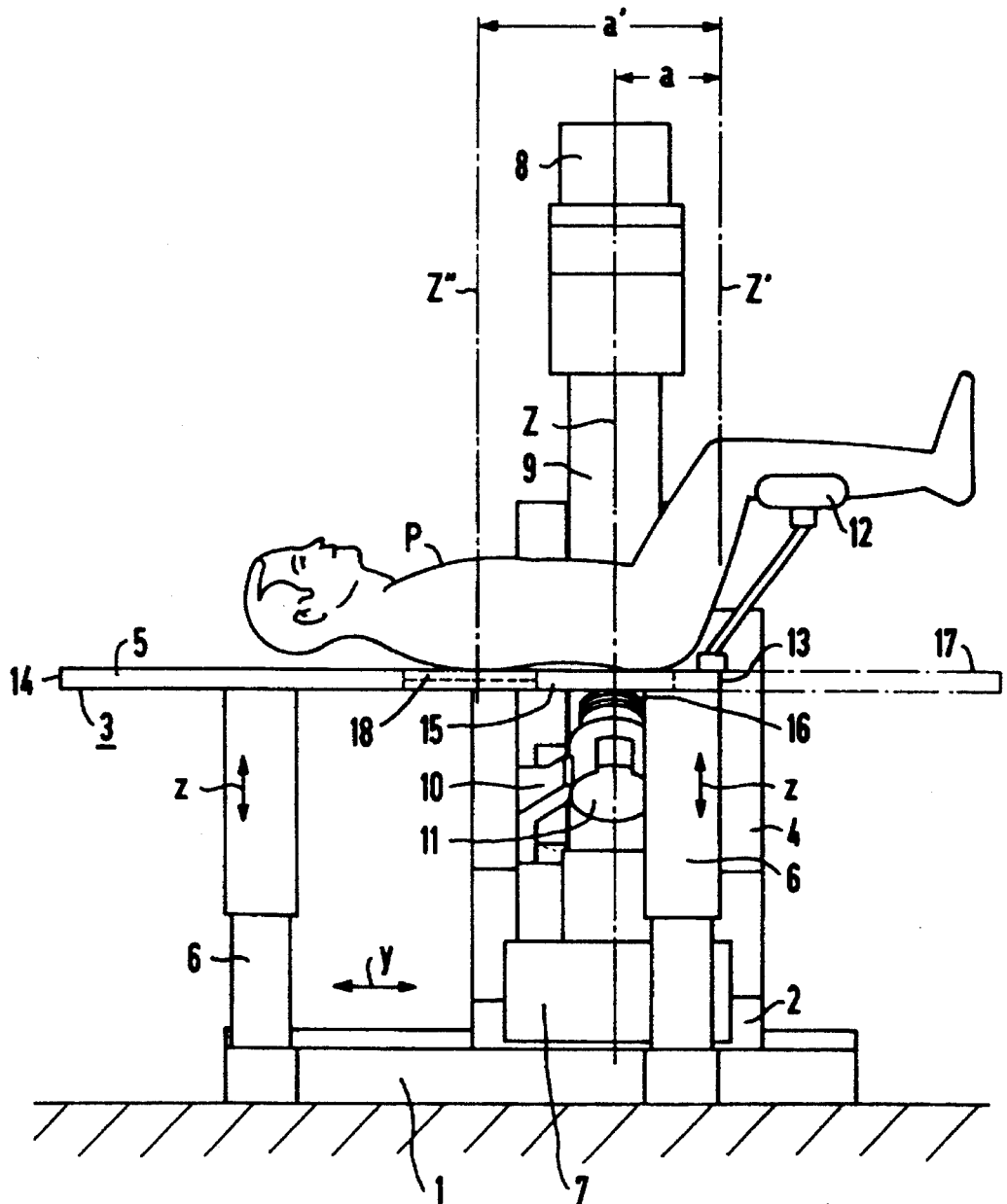
FIG. 1 is a schematic illustration of a side view of the urological workstation of the invention.

The urological workstation of the invention has a base 1 on which a carriage 2 is adjustable in the y-direction that proceeds perpendicularly relative to the plane of the drawing, and thus parallel to the longitudinal axis of a patient support table 3. A carrier part 4 is mounted on the carriage 2 so as to be longitudinally displaceable in the x-direction that proceeds transversely relative to the y-direction and thus transversely relative to the longitudinal axis of the patient support table 3. The support plate 5 of the patient support table 3 is height-adjustable in the z-direction. To this end, the patient support table 3 has two telescoping columns 6 arranged at a distance from one another in the longitudinal direction of the patient support table 3.

An x-ray diagnostics installation is attached to the carrier part 4 for the implementation of urological x-ray examinations. This x-ray diagnostics installation includes an x-ray radiator 7 and an x-ray image intensifier 8 that are attached to the ends of a C-arm 9, opposite one another.

The C-arm 9 is connected to the carrier part 4, in a way that is not shown in greater detail, so that it can be adjusted along its circumference in the direction of the curved double arrow $\alpha$. There is thus the possibility of irradiating a patient on the patient support table 3 from different directions.

For the implementation of an x-ray examination, the patient P is placed in the lithotomy position on the patient support table 3 with the assistance of leg supports 12, as indicated in FIG. 1. In order to be able to examine different regions of the patient, the x-ray diagnostics installation is adjusted relative to the patient support table 3 and, thus, relative to the patient P, so that its central ray Z is shifted between parallel positions. This can ensue by displacing the carriage 2 on the base in the y-direction and/or by adjusting the carrier part 4 on the carrier 2 in the x-direction.

In order also to be able to examine the regions of the urogenital tract that lie close to the perineum of the patient situated immediately above the end edge 13 that limits the patient support table 3 in the direction of its longitudinal axis, the x-ray diagnostics installation can be moved in the y-direction into a first final position wherein the central ray of the x-ray diagnostics installation proceeds through the end edge 13. The corresponding position of the central ray is indicated in FIG. 1 referenced Z'.

In order to examine the entire urogenital track, the x-ray diagnostics installation is adjustable by a dimension of 22 cm in the direction toward the other end edge 14 proceeding from this first final position and vice versa, i.e. in the y-direction. The x-ray diagnostics system is shown in this second final position in FIG. 1. Any desired intermediate positions are possible.

Different regions of the patient P thus can be examined when the patient P is at rest, i.e. is stationary. There is thus no relative motion of the patient with respect, for example, to a urologist seated between the legs of the patient. Once the urologist has found a comfortable position, he can remain in this position regardless of what region of the patient is being examined with the x-ray diagnostics installation.

Figure 2:
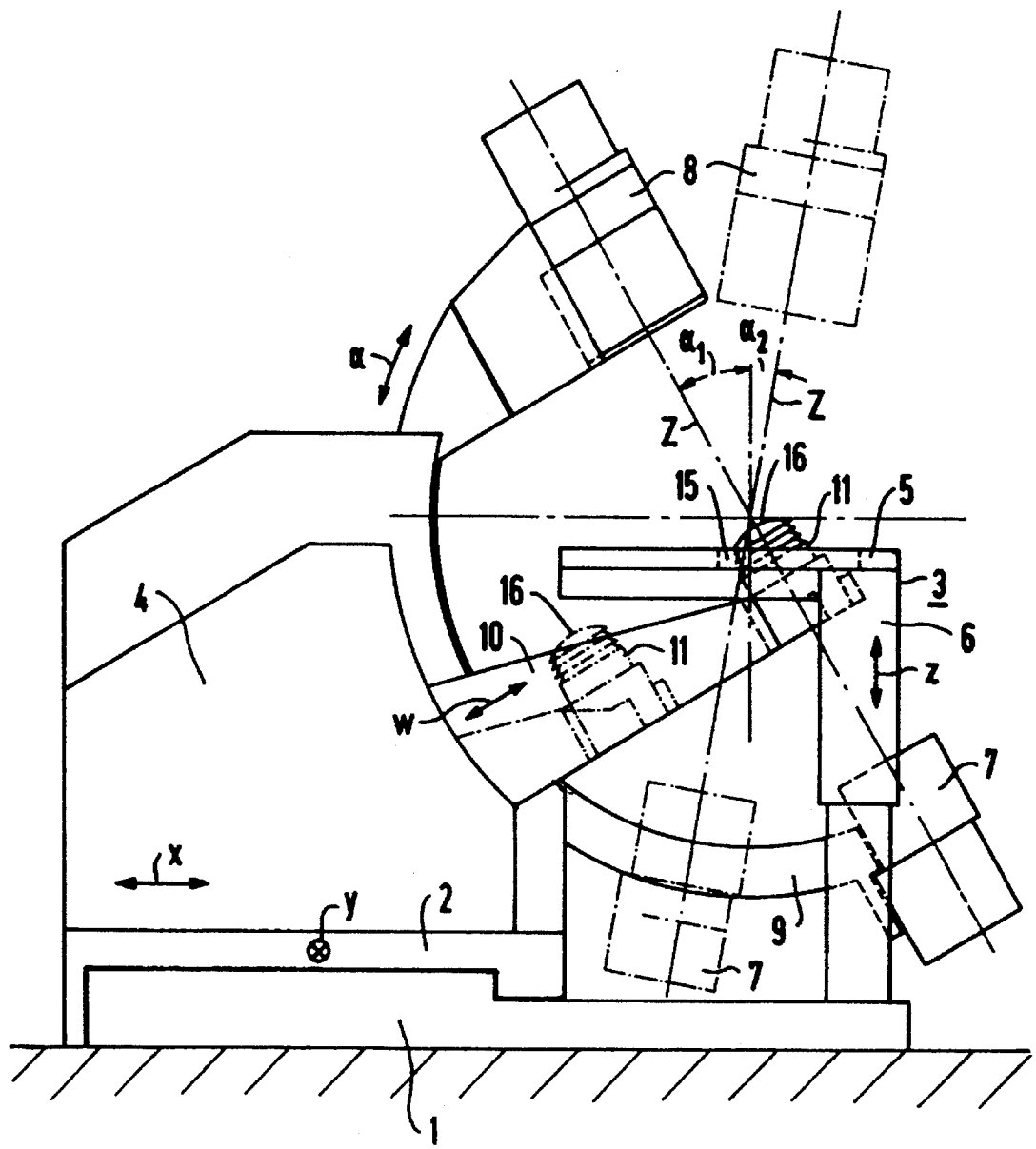
FIG. 2 is an end view of the workstation of FIG. 1, again in a schematic illustration.

The urological workstation of the invention also includes a therapy means. In the exemplary embodiment shown in the Figures, this is a source 11 of focused acoustic waves that is attached to the carrier part 4 with a support 10. By adjusting the support 10 in the direction referenced w in FIG. 2, this source 11 can be optimally adjusted relative to the carrier part 4 from a working position shown in FIG. 2, wherein it projects through a cut-out 15 in the bearing plate 5, into a standby position shown in FIG. 1 (also indicated with broken lines in FIG. 2). The source 11 has a flexible application bellows 16 with which it presses against the body surface of the patient for acoustic coupling during the treatment.

For implementing a treatment with the source 11, this is brought from its standby position into its working position wherein it presses against the body surface of the patient through a cut-out 15 of the patient support table 3 with the flexible application bellows 16 for acoustic coupling.

The region to be treated is located by irradiating the patient from different directions. The corresponding directions of the central ray are indicated in FIG. 1 and describe the angle $\alpha_1$ or $\alpha_2$, with the vertical. The region to be treated is positioned into the active zone of the source 11 (which assumes its working position) on the basis of the information thereby acquired. This occurs by suitable adjustment of the carriage 2 in the z-direction, the carrier part 4 in the x-direction, and the bearing plate 5 in the z-direction.

The source 11 may alternatively be a therapeutic ultrasound source, for example of the type disclosed in greater detail in U.S. Pat. No. 4,526,168, or a pressure pulse source emitting shockwaves, for example of the type disclosed in greater detail in U.S. Pat. No. 4,674,505. These alternatives respectively permit either pathological tissue regions, or stone and bone conditions to be treated. For treating kidney stones, it will generally suffice when the central ray of the x-ray diagnostics installation in the second final position at a distance a of 22 cm from the end edge 13 measured in the longitudinal direction of the patient support table 3. In order to also be able to comfortably treat gallstone conditions, it is expedient when the distance from the end edge 13 is 54 cm, since the region that is relevant for this therapy can then also be portrayed well with the x-ray diagnostics installation. The corresponding dimension a' and the position of the central ray, referenced Z", are shown in FIG. 1.

It is self-evident that the patient P assumes a prone position for the treatment of gallstone conditions. In order to apply the source 11 in the required way, a slide 18, indicated with broken lines in FIG. 1, is displaced such that it closes the opening 15 and instead exposes a different portion of the opening in the bearing plate 5 that is closed by the slide 18 in the operating condition shown in FIG. 1. A table extension 17 can be pulled out if necessary, as indicated by dashed lines in FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A urological workstation comprising:

a support table adapted to receive a patient to be examined, said support table having a longitudinal axis defining a longitudinal direction of said support table and having a length along said longitudinal axis which is less than or equal to approximately 145 cm, said support table having a first end edge which limits said support table in said longitudinal direction;

x-ray diagnostics means for generating an x-ray image of a region of said patient, said x-ray diagnostics means having a central ray;

means for moving said x-ray diagnostics means in a first direction parallel to said longitudinal axis with said central ray being shifted through a plurality of parallel positions and for moving said x-ray diagnostic means in a second direction to a first final position so that said central ray proceeds through said first end edge; and a base to which both said support table and said means for moving said x-ray diagnostic means are attached, and said support table being stationary in said first and second directions.

2. A urological workstation as claimed in claim 1, wherein said support table has a second end edge, opposite from said first end edge and limiting said support table in said longitudinal direction, and wherein said means for moving said x-ray diagnostics means comprises means for moving said x-ray diagnostics means from said first final position toward said second end edge of said support table into a second final position wherein said central ray is disposed at a distance which is greater than or equal to approximately 22 cm from said first end edge of said support table measured in the direction of said longitudinal axis.

3. A urological workstation as claimed in claim 1 further comprising means for administering therapy to said patient while said patient is on said support table, and wherein said x-ray diagnostics means comprises means for locating a region to be treated with said means for administering therapy.

4. A urological workstation as claimed in claim 3 wherein said means for administering therapy comprises an acoustic waves source.

5. A urological workstation as claimed in claim 4 wherein said support table has first and second opposite end edges respectively limiting said support table in the direction of said longitudinal axis, and wherein said means for moving said x-ray diagnostics means comprises means for moving said x-ray diagnostics means to a first final position wherein said central ray proceeds through said first end edge of said support table, and for moving said x-ray diagnostics means from said first final position toward said second end edge of said support table into a second final position wherein said central ray is disposed a distance which is greater than or equal to approximately 54 cm from said first end edge in the direction of said longitudinal axis of said support table.

* * * * *